(12) United States Patent
Miloslavski et al.

(10) Patent No.: US 8,945,161 B2
(45) Date of Patent: Feb. 3, 2015

(54) DEVICE FOR OPENING OCCLUDED BLOOD VESSELS

(75) Inventors: Elina Miloslavski, Stuttgart (DE); Hermann Monstadt, Bochum (DE); Ralf Hannes, Dortmund (DE)

(73) Assignee: Phenox GmbH, Bochum (DE)

( * ) Notice: Subject to any disclaimer, the term of this patent is extended or adjusted under 35 U.S.C. 154(b) by 0 days.

(21) Appl. No.: 13/059,474

(22) PCT Filed: Aug. 19, 2009

(86) PCT No.: PCT/EP2009/006018
§ 371 (c)(1),
(2), (4) Date: Apr. 5, 2011

(87) PCT Pub. No.: WO2010/020408
PCT Pub. Date: Feb. 25, 2010

(65) Prior Publication Data
US 2011/0224707 A1   Sep. 15, 2011

(30) Foreign Application Priority Data
Aug. 19, 2008   (DE) .......................... 10 2008 038 195

(51) Int. Cl.
*A61B 17/22*   (2006.01)
*A61B 17/221*   (2006.01)

(52) U.S. Cl.
CPC ......... *A61B 17/221* (2013.01); *A61B 17/22031* (2013.01); *A61B 2017/22042* (2013.01); *A61B 2017/2212* (2013.01)
USPC .......................................... 606/159; 606/200

(58) Field of Classification Search
USPC .................. 606/159, 170, 180, 191, 198, 200
See application file for complete search history.

(56) References Cited

U.S. PATENT DOCUMENTS

| 6,458,139 | B1 * | 10/2002 | Palmer et al. ................. 606/113 |
| 2002/0165597 | A1 * | 11/2002 | Clerc et al. ..................... 623/1.2 |
| 2005/0021075 | A1 * | 1/2005 | Bonnette et al. ............. 606/200 |
| 2005/0216053 | A1 * | 9/2005 | Douk et al. ................... 606/200 |
| 2006/0235463 | A1 * | 10/2006 | Freudenthal et al. ......... 606/200 |
| 2007/0005104 | A1 * | 1/2007 | Kusleika et al. .............. 606/200 |

\* cited by examiner

*Primary Examiner* — Thomas McEvoy
(74) *Attorney, Agent, or Firm* — Berliner & Associates

(57) ABSTRACT

The invention relates to a device for opening occluded blood vessels, comprising a braided structure (2) on a guide wire (1), said braided structure (2) being securely and permanently attached to the guide wire and consisting of a plurality of filaments (4) arranged in a helical manner and at least at the proximal end combined into a bundle, with the braided structure (2) assuming an elongated form of smaller diameter when subjected to external force while when in unstressed state defining a tubular element of larger diameter closed at least at its proximal end, with the device being provided with restraining/bracing fiber elements (9).

13 Claims, 5 Drawing Sheets

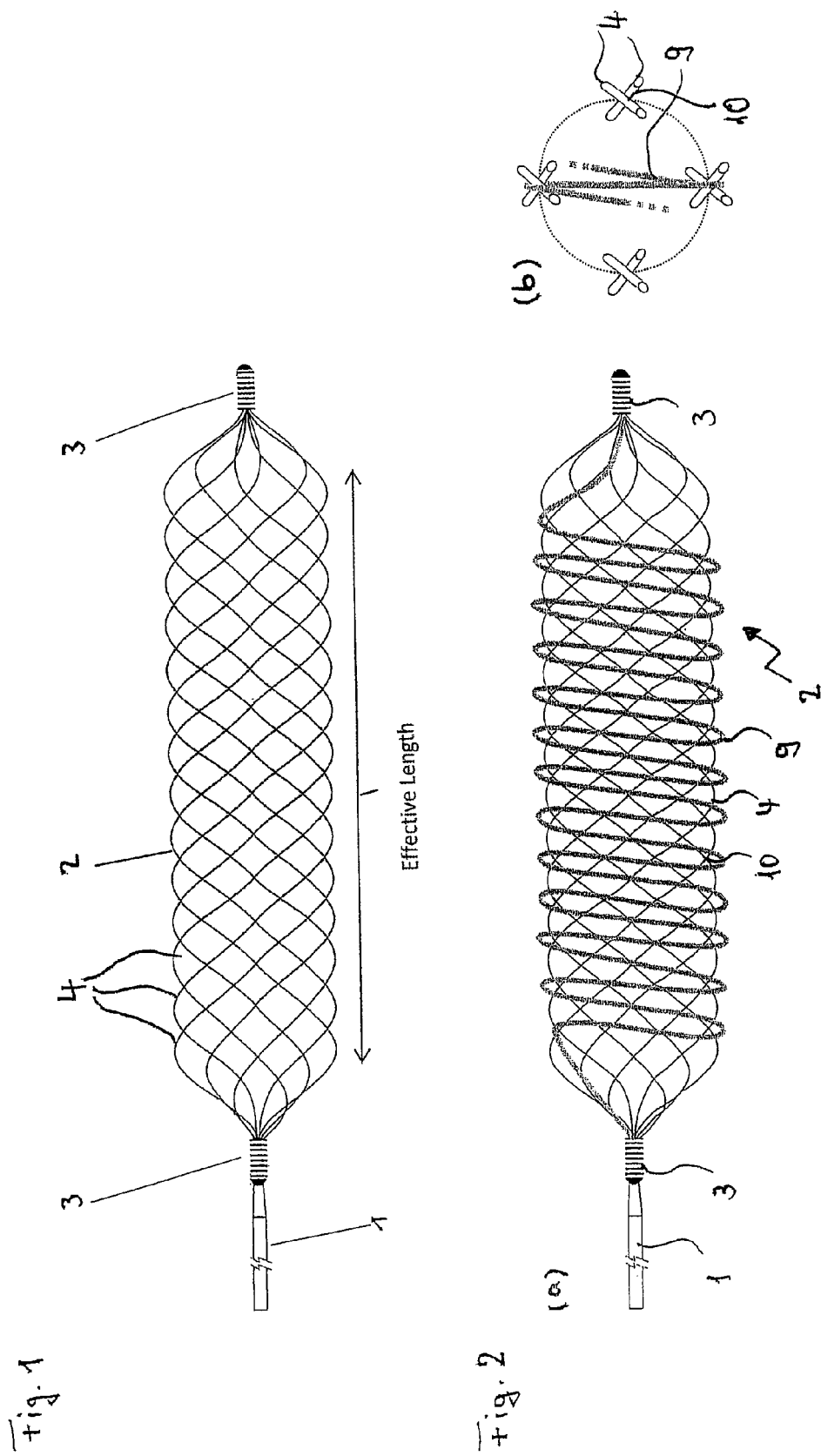

Fig. 6
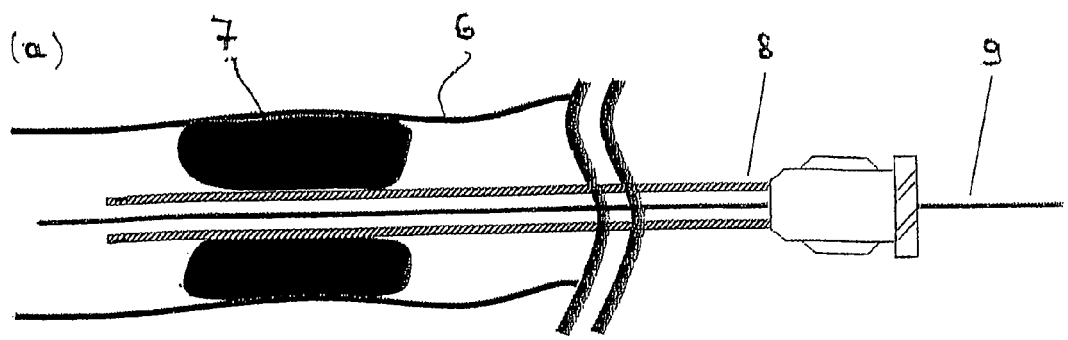
(a)
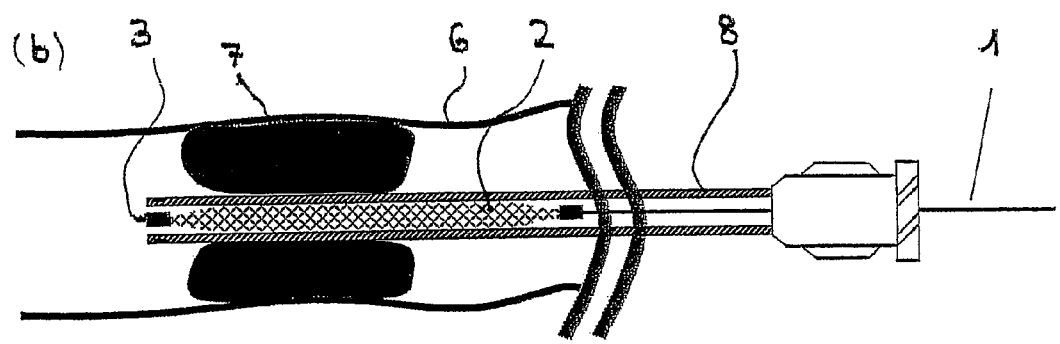
(b)
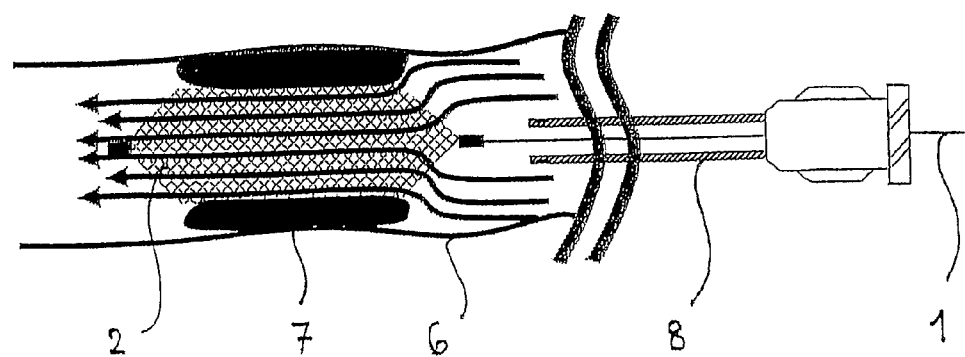
(c)

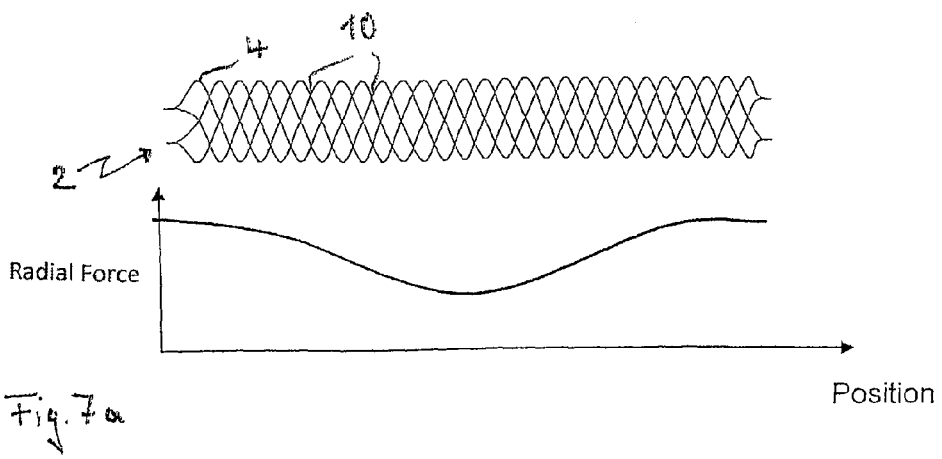
Fig. 7a
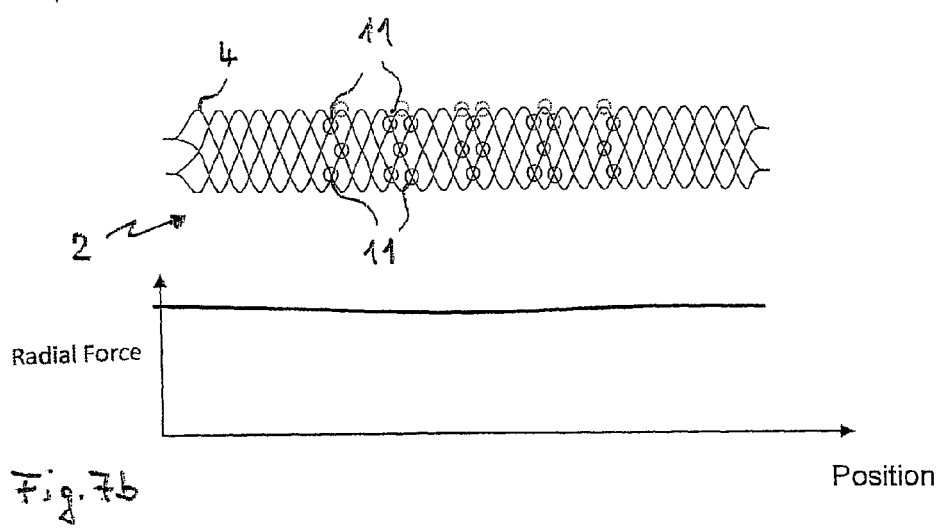
Fig. 7b
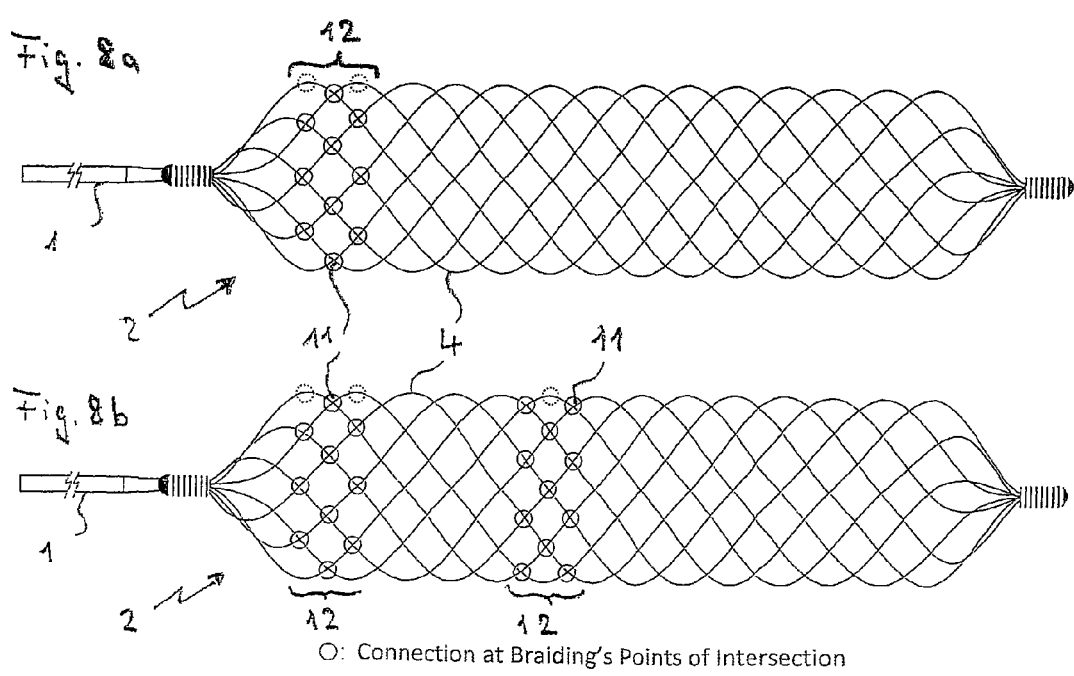
Fig. 8a
Fig. 8b
O: Connection at Braiding's Points of Intersection

DEVICE FOR OPENING OCCLUDED BLOOD VESSELS

The invention relates to a device for the opening of occluded blood vessels, said device being provided with a braided or mesh structure comprising a multitude of filaments and being attached to a guide wire. The braided structure is securely and permanently attached to the guide wire.

Thromboembolic diseases such as cardiac infarction, pulmonary embolism, peripheral thrombosis, organ embolisms etc. are typically caused by a thromboembolism (hereinafter for short thromb or thrombus), i.e. a visco-elastic blood clot comprising platelets, fibrinogen, coagulation factors etc. forming in a blood vessel which it obstructs either wholly or in part. The obstruction of organ arteries also leads to supply of oxygen and nutrients to the associated tissue being interrupted. The disorder of the functional metabolism linked with functional losses is closely followed by a failure of the structural metabolism resulting in the relevant tissue becoming destroyed (infarction). Organs most frequently affected in this way are the heart and the brain. Nevertheless, the arteries of the limbs as well as pulmonary arteries are also impaired. Venous thromboses and thromboembolic occlusions are frequently occurring in the leg and pelvic veins. The disease pattern of the thrombotic occlusion of an intracranial sinus may lead to severe intracerebral hemorrhage due to a failure of venous drainage of brain tissue.

In view of the severity of the disease patterns associated with thromboembolism and the prevalence rate of such diseases various techniques have been developed aimed at dissolving or removing thrombi.

It is known in this context to treat such patients with thrombolytic agents such as streptokinase or urokinase or anticoagulants intended to achieve thrombolysis or limit the growth of thrombi. Since treatment methods of this kind are usually very time consuming they are frequently combined with invasions aimed at reducing the size of or removing the thrombus or embolus mechanically.

Aside from open surgical operations prior art techniques more and more embrace the use of transluminal or endovascular, catheter-guided interventional therapy methods because these are of less invasive nature. It is thus known to remove the thrombus from the patient's body by means of vacuum producing suction catheters or mechanically using catheters provided with capturing cages, helixes, hooks, brushes or similar elements; refer to U.S. Pat. No. 6,245,089 B1, U.S. Pat. No. 5,171,233 A1, WO 2006/021407 A2, Thomas E. Mayer et al., Stroke 2002 (9), 2232.

Disadvantages associated with the known transluminal devices are that with said devices it is not always possible to remove the thromb or remove it completely and, moreover, there is a risk of the thromb or fragments of it being released into the blood stream thus passing on to vessels of smaller lumen which are more difficult to reach and treated. Moreover, the interrupted or insufficient flow of blood leads to serious consequential damage which even increases the longer the interruption prevails.

In such a situation there is need for a device by means of which, in the event of thrombi that cannot be removed, or cannot be removed completely or quickly enough, the flow of blood can be restored at least partially and temporarily to gain time for an appropriate intervention, or possibly use such a device with a view to exerting effects on the thrombus so that it can be eliminated altogether or in part.

According to the invention this objective is achieved by providing a device for opening occluded blood vessels, comprising a braided structure on a guide wire, said braided structure being securely and permanently attached to the guide wire and consisting of a plurality of filaments arranged in a helical manner and at least at the proximal end combined into a bundle, with the braided structure assuming an elongated form of smaller diameter when subjected to external force while when in unstressed state defining a tubular element of larger diameter closed at least at its proximal end, with the device being provided with restraining/bracing fiber elements.

In practice the inventive device is advanced to the thrombus in a customary micro-catheter suitable for the intended purpose. Following this, the catheter penetrates the thrombus and is then retracted causing the inventive device to be liberated and thus being permitted to assume a larger diameter in unstressed condition as compared to its compressed state when subjected to the external force exerted by the catheter wall. In this state the braided structure defines a tubular body which expands to an extent limited by the vessel wall and/or thrombus. The prestressing of the braided structure causes the thrombus to be compressed and an at least partial flow of blood through the braiding structure is thus ensured.

At the same time the braided structure with restraining fibers serves a filtering function. Parts of the thrombus which are detached when the braided structure expands are collected within the braided structure at its distal end. The stripping effect can be intensified by appropriately moving the braided structure (axial or turning movement) to perform a peeling or scraping action so that at the end of the treatment the device which then contains the accumulated fragments of the thrombus can be drawn back into the catheter and removed from the body. In the event the thrombus cannot be eliminated completely at least a channel passage remains open through which the perfusion of downstream vessel sections may take place.

Results initially obtained show that the inventive device enables thrombi, in particular also thrombi located in vessels of small lumen, to be reached and perforated. The guide wire makes it possible for the device to be easily moved also in convoluted vessel segments and keeps the overall diameter of it small, but in particular the device diameter that cannot be varied. The braided structure and the fibers are of suitable design to hold back and retain thrombus fragments.

The fibers forming the restraining/bracing system consist of materials suitable for medical purposes, for example polyamide, polyester or polypropylene. Polyamide fibers are preferred.

By restraining/bracing fibers a spatial fiber structure is meant that extends through at least part of the interior space of the braided structure. The restraining fibers forming an additional spatial mesh structure inside the braided structure serve to reliably collect and retain parts of the thrombus that have become detached when the device has expanded. On the other hand, this spatial mesh structure shall be open enough to allow the passage of blood through the braided structure from proximal to distal.

When reference is made to the term „restraining fibers" this is meant to describe an arrangement of fibers that extend through the interior space of the braided structure from filament to filament. The fibers may be under a certain amount of tension when the braided structure has been fully expanded which may be expedient but is not obligatory. To all intents and purposes the fibers may also extend through the interior free from tension.

Contrary to the state-of-the-art brush structures the restraining fibers offer the advantage that a central wire otherwise needed for bristles attachment can be dispensed with. In this way the volume can be reduced and the device designed spatially smaller, especially with respect to its diameter, so that it can also be inserted into vessels of finer configuration.

Since the device according to the invention is not intended to serve as implant it is to be understood that guide wire and distal element are non-detachably connected with each other. In due course the device possibly containing fragments is retracted into the micro-catheter or an additional guide catheter in which it is then removed from the body of the patient.

The braided structure consists of a plurality of helically extending filaments. The number of braided wires may vary broadly, for example range between 4 and 128, but a number of between 6 and 16 filaments is sufficient basically. In non-stressed or tension-free condition the braided wires assume the shape of a tube the walls of which are formed by the filaments, with in any case the proximal end of the tube, but possibly the distal end as well, being closed off by the converging filaments. Proximal in this context denotes the end of the braided structure nearest to the attending physician, the micro-catheter and/or the guide wire, whereas distal refers to the end furthest away from them.

The braided structure preferably consists of metal filaments exhibiting restoring resp. shape-memory properties. This may be steel suitable for medical uses having good spring characteristics, but in particular the structure may consist of filaments made of shape-memory alloys such as nitinol for example. In particular, the filaments have a diameter ranging between 0.01 and 0.2 mm.

Proximally same as distally the individual filaments are combined into a bundle securely attached to the guide wire, for example by welding, bonding or crimping. Preferably, the bundle is held together by a sleeve which at the same time serves as radiopaque marker and consist, for example, of a platinum metal or a platinum metal alloy (Pt/Ir).

The filament bundle will usually be located centrally, i.e. on the rotational axis of the braided structure. In special cases, for example to improve maneuverability, the bundle may expediently also be arranged off-center, approximately at the height of the wall of the braided structure.

Inside the catheter the braided structure assumes a compressed and elongated form of smaller diameter as determined by the catheter diameter in which it can be transported to the place of intervention. As soon as the braided structure is released from the catheter it expands to an extent permitted by the surrounding area until it assumes a maximum larger diameter that may, for example, amount to 10 mm. As a rule the braided structure will not expand and cannot unfold completely because it will come into contact with the vessel wall and/or thrombus. This is also considered expedient in order to make full use of the internal tension of the braided structure to enable the thrombus to be compressed or divided. The maximum force exerted by the braided structure against the vessel wall when expanding should not exceed 0.3 N in a single direction to rule out injuries of the vessel wall. Expediently, this should be 0.1 to 0.3 N over an effective length of 20 mm.

Stent-like braided structures—especially those with distally and proximally connected braiding wire ends—show different radial force ranges when regular braiding patterns are provided. In a static state of rest the radial force is usually lesser pronounced in the middle than in the end areas. This, inter alia, is due to the individual wires of the braiding pattern being arranged above and underneath each other without a connection having been provided between them. Moreover, radial forces generated on the proximal side are reduced by the pull movement that takes place in proximal direction because the centrally arranged connection causes the individual wires to be pulled towards the center of the braiding (application, dynamic state).

If individual braiding wires crossing each other are connected—especially those arranged on the circumference adjacent to each other—this increases the radial forces of the entire device. It is not necessary at all in this context to provide connections at all points of intersection, all the more so as this would impair the flexibility of the device.

By appropriately arranging the number and location of the connections at the intersection points in relation to the length and circumference, the radial forces exerted by the braiding can be adjusted. Especially in the proximal and central area increasing the radial forces is often desirable. For this purpose and preferably in the proximal and central part of the braiding but not at its distal end connections are made at individual points where filaments intersect. Preferably, the points of intersection connected with each other are arranged on ring segments on the proximal and/or in or up to the central part of the braiding structure.

At the points of filament intersection thus to be attached the connections may be made by providing weld spots or bonding/gluing spots. Weld spots may be generated by laser welding or pressure resistance welding methods. Soldering methods may also be employed.

Connections may as well be made by enlacing and/or knotting the points of intersection together using wire or thread material. Such wire material may in particular be nitinol but platinum, platinum alloys and stainless steel may also be used. As thread materials polyamides may for example be employed. For this purpose, the restraining fibers may advantageously be used.

In general, the inventive braiding structures are 10 to 70 mm long (effective length) and have an expanded outer diameter of between 1 and 10 mm, preferably 15 to 30 mm long with diameters ranging between 3 and 6 mm. It is expedient to provide braiding structures having diameters appropriate to the varying vessel diameters.

As guide wire a customary guide wire may be employed that consists of an elastic material, for example steel suitable for medical purposes, said wire being of tapered configuration especially at the distal end, ground so as to be thinner and thus facilitate connection to the filament bundle and sleeve and to have a softer and more flexible wire distally. A covering or coating of the guide wire, particularly applied in the distal area, may be useful, for example in the form of a PTFE tubing.

The inventive device is provided with fibers extending radially through the interior space and from filament to filament. Such fibers extend, in particular, from point to point of filament intersection over the entire effective length or part of it, especially in the distal area.

In principle, the fibers may be tightened or extend through the interior space in any desired manner. However, preferred is here to arrange them in regular patterns of raylike or starlike configuration as viewed in the longitudinal direction of the braiding structure. In this way sufficiently dense networks of fibers can be produced with a view to retaining thrombi without the flow of blood being unduly impeded.

Preferred are restraining fiber configurations extending in a zig-zag fashion longitudinally through the braiding structure, with said fibers being secured to opposite points of filament intersection and for the most part extending radially through the longitudinal axis of the braided structure. Additionally preferred are configurations that provide for the fibers to be attached to points of filament intersection not located opposite each other and form perpendicularly to the longitudinal axis of the braided structure regular starlike patterns having an internal channel structure. In this case for example, the fibers as viewed in a single plane extend from one point of intersection each to the next but one or fourth etc. with all intersecting points that are lying in a plane being included. In the first case a raylike structure of several fibers running in longitudinal direction is created through the fibers extending radially in longitudinal direction, in the second case a number of starlike structures is produced in a plurality of planes of the braided structure.

Both the braided structure of the filaments and the fibers extending/tightened therein are suited to serve a filtering purpose to retain fragments detached from or stripped off the thrombus. Furthermore, the device is permeable enough to warrant that at least a partial flow of blood can pass through the thrombus throughout the entire application period and thus ensure the perfusion of downstream tissue.

To improve the filtering efficiency it may be expedient to increase the density of the filaments arranged in the distal part of the braided structure, for example by providing for a more narrow configuration of and reducing distance between the helically coiled and, as the case may be, braided elements, or by providing additional filaments or incorporating fibers into the wall of the braided structure. Such a denser structure of the braiding may, for instance, be only created in a partial area at the closed end of the braided structure but may also extend over a distal part of the wall of the braided structure.

It is to be understood that the braided structure with restraining fibers including a guide wire as provided for within the scope of the invention may be used without this guide wire as a temporary or long-term implant. For this purpose the guide wire can be designed so as to be detachable.

The invention is explained in more detail by way of the enclosed figures where

FIG. 1 shows a braided structure according to the invention;

FIG. 2 shows a braided structure according to FIG. 1 with restraining fibers in place;

FIG. 6 illustrates the functioning of the device according to the invention;

FIG. 7 shows the influence of intersecting points in the braiding of an inventive device on the radial force of the device; and FIG. 8 shows two embodiments of an inventive device with proximal (a) and proximal plus central (b) arrangement of the points of intersection.

Figure 3:
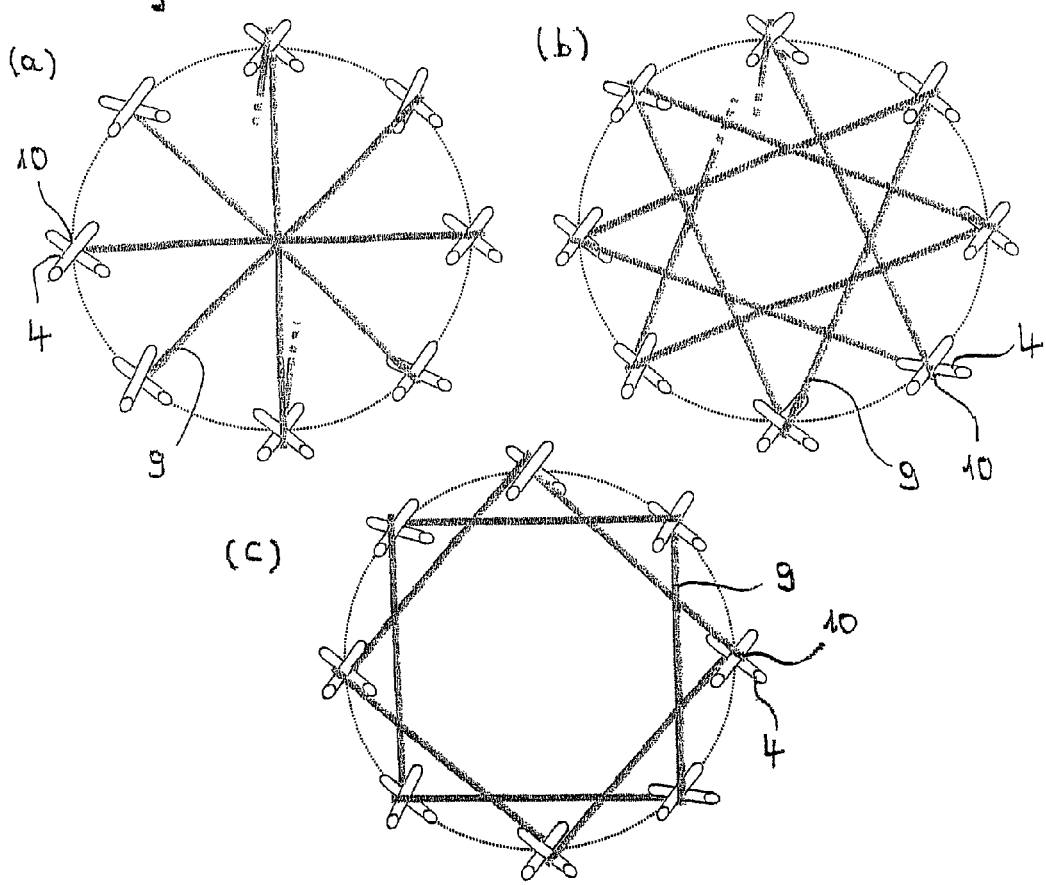
FIG. 3 illustrates further variants of an inventive device with different fiber arrangements.

FIG. 1 shows a preferred embodiment of the device in accordance with the invention comprising a guide wire 1, a braiding structure 2 as well as two radiopaque markers 3. The braiding structure consists of a total of eight filaments 4 extending primarily in parallel and helical coils thus assuming the shape of a tubular body. At the distal and proximal ends the filaments 4 converge in the rotational axis of the braiding structure to form a bundle, with both bundles held together by radiopaque markers 3 in the form of a sleeve. The guide wire 1 terminates in the proximally arranged sleeve, said wire being ground distally so as to have a tapered shape with a view to achieving increased flexibility.

In all embodiments the individual filaments 4 are braided preferably according to an " above 1/below 1" pattern, which means that at its intersecting points one filament 4 runs alternately over and underneath other filaments. An "above 2/below 2" arrangement is also conceivable.

As a result of the filament configuration the braided structure 2 remains open at its distal and proximal end while it is restricted over its length due to the vessel wall surrounding it. Therefore, in the longitudinal direction of the braided structure blood is allowed to pass through the structure.

FIG. 2a shows an inventive device comprising braided structure 2 and individual filaments 4 extending in a helical manner and being intertwined with each other. Between the marker sleeve 3 a fiber 9 extends from point of intersection to point of intersection, with said fiber being arranged essentially in a single plane across the entire braiding 2.

FIG. 2b is a schematic cross sectional view showing the intersecting points of filaments 4 and the fiber extending between two points of intersection. The fiber or fiber substance may consist of a material suited for medical purposes, for example a polyamide, polypropylene or polyester filament.

FIG. 3 depicts three variants of how fibers are arranged within a braiding structure 2. According to FIG. 3a the fiber extension is longitudinal, with the fibers 9 each being arranged between the oppositely located points of intersection 10 of two filaments 4 and extending through the center of the braided structure from proximal to distal. A total of four fibers extending as per the fiber arrangement illustrated in FIG. 2 will, when seen in the longitudinal direction of the device, produce a raylike pattern.

FIG. 3b shows fibers extending within a single plane of braiding structure 2, where the fibers extend from an intersecting point 10 to every fourth point of intersection so that within a plane a starlike pattern is achieved which allows a central channel to be formed. After all intersecting points in a given plane are interconnected the fibers attach to the intersecting points of the next planes where an identical pattern is created.

In FIG. 3c a structure is illustrated that allows for a greater inner channel, with fibers 9 being stretched from a given intersecting point 10 to the next but one. Here as well a starlike pattern of fibers is produced in each plane. In this case and after having connected all points in a given plane the fibers may change over to the next plane; however, arrangements are conceivable where only the intersecting points in a given plane are interconnected by means of one or several fibers and new fibers are used for the adjacent planes.

It shall also be understood that the illustrated pattern of restraining fibers may extend over the entire length of the braiding structure 2 but it may also be arranged over a partial length of it only, preferably the distal area.

Figure 4:
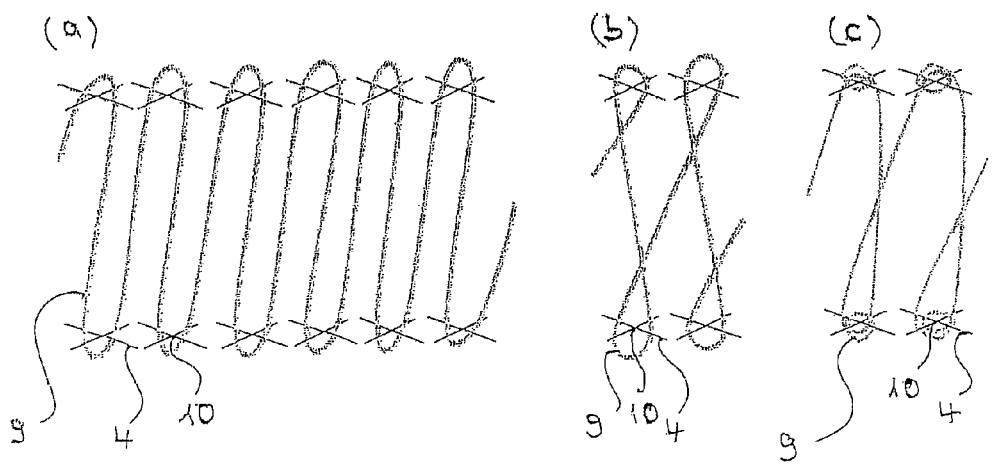
FIG. 4 shows three variants of fiber attachment at points of intersection.

FIG. 4 shows three variants of how such a fiber 9 is arranged between intersecting points of filaments 4 over a portion or the entire effective length of a braiding structure 2. The fiber winds around the points of intersection enlacing them half (a). As per variant (b) the fiber winds around the intersecting point in full which improves fixation of fibers and also results in the points of intersection of filaments 4 to be better secured. As per variant (c) fiber 9 winds 1½ times around each point of intersection 10 of the filaments 4.

Figure 5:
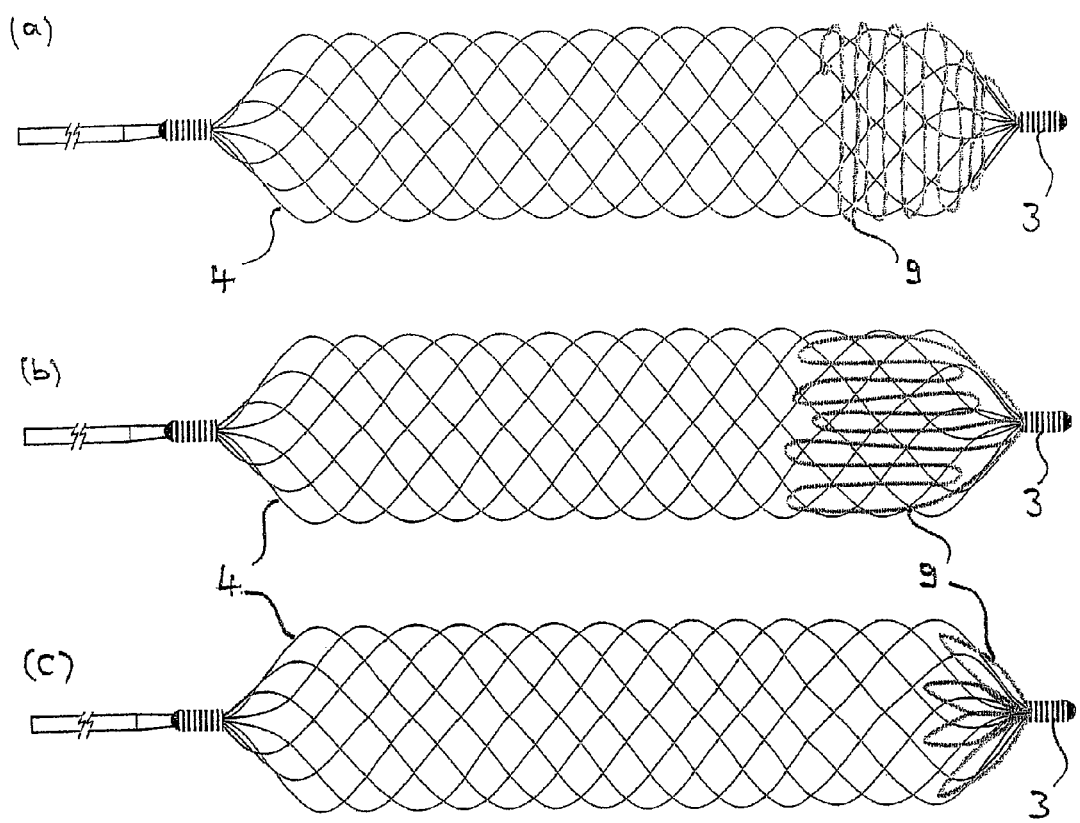
FIG. 5 depicts variants of a braiding structure where the distal ends are of dense configuration.

FIG. 5 shows three variants of a distally densified braided structure 2 where fibers 9 with a view to densifying the "shell" are distally integrated into structure 2, and as can be seen from FIG. 5a the fiber 9 runs alternately over a filament 4 and then under filament 4. As per FIG. 5b fibers 9 extend to and fro axially parallel over the circumference and in this way create a denser shell, with said fibers being intertwined with filaments 4 in this case as well.

As is shown in FIG. 5c additional wires are integrated into the marker sleeve 3, said wires extending in loop-shaped configuration with the loops opening up in a blossom-like fashion.

It is to be understood that filaments 4 may also be readily arranged so as to achieve a denser braiding configuration in the distal area.

Details of how the inventive device can be applied can be seen from FIG. 6. A thrombus 7 is located in a blood vessel 6, said thrombus having already been penetrated by micro-catheter 8. Inside the micro-catheter an insertion wire 9 is arranged by means of which the micro-catheter has been moved to the application site (FIG. 6a).

From FIG. 6b it can be seen that the micro-catheter 8 accommodates the inventive braiding structure 2 with distal and proximal markers 3 on insertion wire 1. The braiding structure has assumed a compressed and stretched shape, i.e. its diameter is significantly smaller than its maximum diameter.

FIG. 6c shows the device in accordance with the invention after the micro-catheter 8 has been drawn back. The braiding structure 2 has assumed an expanded and upright form inside the thrombus and in this manner pressed it against vessel wall 6. Now perfusion is restored and blood can pass through the expanded braiding structure 2 as indicated by the arrows shown in the figure.

FIG. 7 shows the influence of filaments connected with each other via points of intersection on the radial force of a braiding. FIG. 7a illustrates the braiding 2 consisting of filaments 4 (only the front half of the braiding has been shown) without points of intersection 10 being connected with each other. With maximum radial forces exerted at the connected ends of the braiding the radial force continuously decreases and reaches its minimum in the center.

As can be seen from FIG. 7b radial forces arising in the central area significantly increase as a result of connections (e.g. produced by welding or bonding) 11 provided at points of intersection 10.

FIG. 8a illustrates an inventive device comprising a guide wire 1, a braiding structure 2 and connection points 11 arranged on some of the braiding's points of intersection. The connections between braiding filaments 4 are not shown in detail but consist preferably of nylon threads knotted around the filament crossing points. Restraining fibers for the device, as they are provided for by the present invention, have not been shown.

Using nylon both on points of intersection and as fiber material offers advantages in terms of thrombogenicity, i.e. thrombi located in the vessel are bonded and can be eliminated without difficulty.

In the embodiment illustrated in FIG. 8a the points of intersection 11 are all located in a ring-shaped segment 12 at the proximal end of the device. FIG. 8b shows a variant where the intersecting points are clustered in two ring-shaped segments 12, that is at the proximal end and in the central area of the device. Connected intersecting points as they are distributed over the circumference produce a stiffer cylinder section which is viewed beneficial both when the device is expanded and when a thrombus is extracted from a vessel by pulling the device backwards.

The same applies of course analogously to the stiffening of braided stents by means of connections made at intersecting points. However, using thrombogenic materials for implants is inadmissible.

It is to be understood that the design by means of which the radial forces of such devices are increased is not only of significance to devices provided for by the present invention but in principle applies to all braiding structures inserted into the body, for example braided stents as they are in particular used in the field of neuroradiology.

The invention claimed is:

1. Device for opening occluded blood vessels, comprising a braided structure (2) on a guide wire (1), said braided structure (2) being securely and permanently attached to the guide wire and consisting of a plurality of filaments (4) arranged in a helical manner and at least at the proximal end combined into a bundle, with the braided structure (2) assuming an elongated form of smaller diameter when subjected to external force while when in unstressed state defining a tubular element of larger diameter closed at least at its proximal end, characterized in that the device is provided with restraining/bracing fiber elements (9), wherein the fibers (9) within the braided structure (2) form a spatial structure and attached directly to points of intersection (10) of the filaments (4) and extend through the interior of the braided structure (2) in a zig-zag fashion between oppositely arranged points of intersection (10) of the filaments (4).

2. Device according to claim 1 comprising 6 to 16 filaments (4).

3. Device according to claim 1, characterized in that the filaments (4) consist of a shape-memory alloy, in particular of nitinol.

4. Device according to claim 1, characterized in that the filaments (4) at least at the proximal end converge centrically or eccentrically.

5. Device according to claim 4, characterized in that the filaments terminate in sleeves (3) which are also designed to serve as radiopaque markers.

6. Device according to claim 1, characterized in that the braiding structure (2) is of densified configuration distally, preferably through incorporated fibers (2).

7. Device according to claim 1, characterized in that the restraining fibers are arranged only in the distal area of the braided structure.

8. Device according to claim 1, characterized in that the fibers (9) extend in zig-zag fashion between oppositely arranged points of intersection (10) of filaments (4) longitudinally through the braiding structure (2).

9. Device according to claim 1, characterized in that the fibers (9) extend between non-neighboring points of intersection (10) and filaments (4) in a plane perpendicular to the longitudinal direction of the braided structure (2).

10. Device according to claim 1, characterized in that the braided structure (2) is adjusted to a force exerted towards a vessel wall of maximum 0.3 N over an effective length of 20 mm.

11. Device according to claim 1, characterized in that the braided structure (2) has filaments (4) connected with each other at points of intersection (10).

12. Device according to claim 11, characterized in that it has been provided in the proximal and/or central area with filaments (4) connected with each other at points of intersection (10).

13. Device according to claim 11, characterized in that the filaments (4) at points of intersection (10) are welded with or bonded to each other or knotted together by means of additional fiber or wire material.

* * * * *